United States Patent [19]

Suzuki et al.

[11] Patent Number: 5,004,928
[45] Date of Patent: Apr. 2, 1991

[54] PRINTING METHOD IN WHICH BOTH SIDES OF THE RECORDING SHEET ARE INSPECTED AND APPARATUS THEREFOR

[75] Inventors: Akio Suzuki, Yokohama; Yoshihiro Takada, Kawasaki; Masami Izumizaki, Tokyo; Toshimitsu Danzuka, Tokyo, all of Japan

[73] Assignee: Canon Kabushiki Kaisha, Tokyo, Japan

[21] Appl. No.: 337,376

[22] Filed: Apr. 13, 1989

[30] Foreign Application Priority Data

| Apr. 18, 1988 | [JP] | Japan | 63-095063 |
| Apr. 18, 1988 | [JP] | Japan | 63-095064 |
| Apr. 18, 1988 | [JP] | Japan | 63-095065 |
| Apr. 18, 1988 | [JP] | Japan | 63-095066 |
| Apr. 18, 1988 | [JP] | Japan | 63-095067 |

[51] Int. Cl.$^5$ .................................. G01N 21/86
[52] U.S. Cl. .................................. 250/559; 356/429
[58] Field of Search ............... 250/559, 571, 235, 236; 356/429

[56] References Cited

U.S. PATENT DOCUMENTS

| 4,284,356 | 8/1981 | Heilman | 250/559 |
| 4,352,988 | 10/1982 | Ishida | 250/559 |
| 4,723,072 | 2/1988 | Naruse | 250/559 |
| 4,760,271 | 7/1988 | Brenholdt | 250/559 |
| 4,779,988 | 10/1988 | Horiguichi | 250/571 |

Primary Examiner—David C. Nelms
Attorney, Agent, or Firm—Fitzpatrick, Cella, Harper & Scinto

[57] ABSTRACT

According to a method and apparatus for detecting a kind of a recording sheet, a light source for emitting a beam on the recording sheet and a photosensitive element for detecting an amount of beam are used. The photosensitive elements located at predetermined positions are caused to detect amounts of beams reflected by upper and lower surfaces of the recording sheet. The kind of upper or lower surface of the recording sheet is discriminated on the basis of a difference between the amounts of beams reflected by the upper and lower surfaces or one of the amounts of beams.

6 Claims, 11 Drawing Sheets $0° < \theta1 = \theta2 < 90°$ $0° < \theta 3 < 90°$

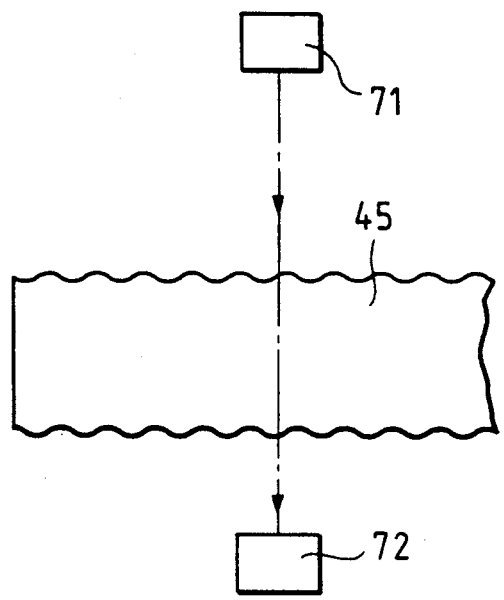
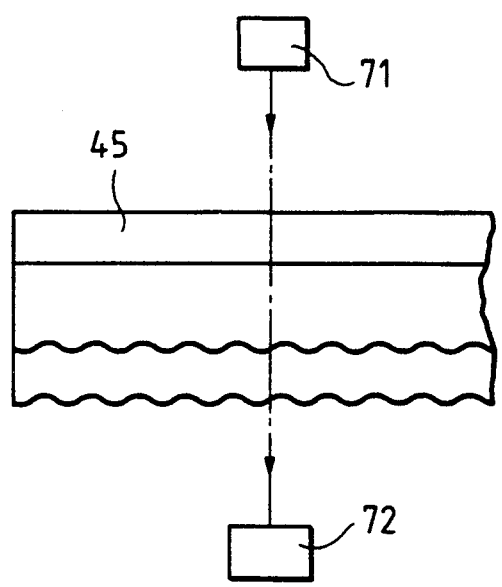
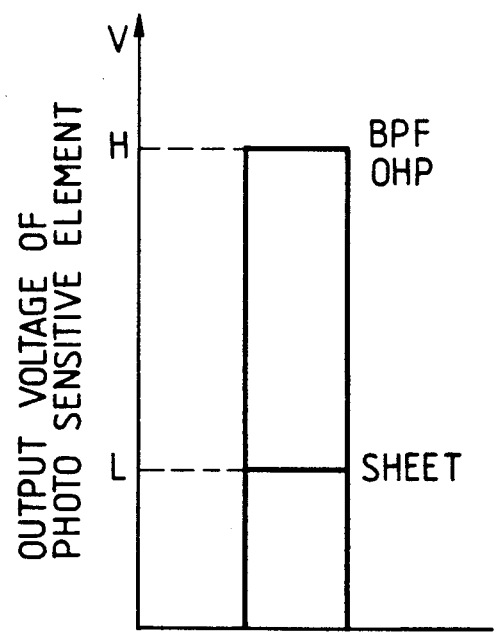

PRINTING METHOD IN WHICH BOTH SIDES OF THE RECORDING SHEET ARE INSPECTED AND APPARATUS THEREFOR

BACKGROUND OF THE INVENTION:

1. Field of the Invention

The present invention relates to a printing method and an apparatus therefor which can be suitably used in a printer, a copying machine, and a facsimile machine.

2. Related Background Art

Paper, an OHP (overhead projection) sheet, and a BPF (back print film) are selectively used as recording sheets (recording media) in a recording apparatus such as a printer and a facsimile machine in accordance with a recording scheme, a required image quality, and an application purpose of a recorded product.

Paper is generally an opaque sheet, and has rough surfaces and is less glossy as compared with other materials such as a plastic film although many kinds of paper slightly vary in gloss and ink absorbing properties depending on their quality or between the upper and lower surfaces.

The OHP sheet has a recording (printing) surface or recording surfaces obtained by forming a coating or coatings on one or both surfaces of a light-transmitting plastic film such as a polyester sheet.

The BPF is prepared such that an ink absorbing layer and an ink transport layer are formed on the lower surface of a base layer consisting of a transparent plastic film, and a recorded image formed in the ink absorbing layer with ink drops injected from the ink transport layer (i.e., the lower surface) side is observed through the base layer (i.e., the upper surface).

The BPF can protect the image with high quality. Recording is performed from the lower surface on the basis of reversed image data obtained by mirror-converting image information.

In addition to real and mirror image modes in which recording is performed from the upper surface of a sheet, the recording (printing) modes include a BPF mode for performing printing on the BPF or the like from its lower surface. The recording modes are employed in correspondence with at least one kind of recording sheet.

The kinds of recording sheets must be limited to a given or predetermined range in accordance with types of recording apparatuses or recording modes set in a given recording apparatus.

In a conventional recording apparatus, the kind of recording sheet is visually or tactually checked by a user, and necessary operations such as setting of a printing mode are manually performed, thus resulting in cumbersome operations and checking errors.

Although a conventional apparatus for discriminating normal paper from a specific sheet such as an OHP sheet is proposed, the kinds of sheets to be discriminated are limited, an installation space is also limited, and handling efficiency is poor.

Information is often printed on the upper or lower surface of a recording sheet or both surfaces. Appropriate recording (printing) cannot be performed unless the upper or lower surface of the sheet such as the BPF and a one-side coated OHP sheet is properly set. In addition, if the paper side is reversed, a real (although nonstandard) or a mirror image is undesirably formed.

In the conventional recording apparatus, the user judges the kind of recording sheet and the difference between the upper and lower surfaces of the recording sheet. Therefore, the recording operation is cumbersome and may result in erroneous judgment.

Printing can be performed on either surface of the normal paper (paper sheet). Printing of the OHP sheets is allowed for only the upper or lower surface or both the upper and lower surfaces depending on their types. When the surface of the BPF sheet is reversed, printing is not often allowed.

As described above, the printing apparatus has three cases depending on kinds of recording sheets: a case in which printing can be performed on either surface of the recording sheet; a case in which printing on the upper surface is standard but printing can be performed even on the lower surface; and a case in which no printing can be performed when the surface of the recording sheet is reversed.

Even if the surface of the recording sheet is reversed, the operator does not often notice it, resulting in an operation error.

A conventional recording apparatus often includes a means for discriminating normal paper from a specific sheet (e.g., an OHP sheet). In this case, when the specific sheet is loaded, the apparatus detects it as an NG recording medium. Therefore, freedom in recording sheet selection is limited, the range of printing functions is also limited, and handling efficiency is poor.

In recent years, a multi-functional recording apparatus (especially, a color image recording apparatus or the like) is available in which the various kinds of recording sheets are used to perform recording in the various recording (printing) modes.

Unless recording sheets are properly set, printing errors occur. Therefore, a variety of applications such as printing of different recording sheets in different printing modes cannot be achieved.

SUMMARY OF THE INVENTION:

It is an object of the present invention to provide a printing method and an apparatus therefor, which eliminate the conventional drawbacks described above.

It is another object of the present invention to provide a method of easily detecting a kind of recording sheet, wherein the kinds of recording sheets can be accurately detected, and almost no limitations are imposed on the kinds of sheets to be used and their storage location.

It is still another object of the present invention to provide a method of detecting a kind of recording sheet and an apparatus therefor, wherein operation errors in recording processing of a recording apparatus having a plurality of recording modes can be eliminated, the range of selection of recording sheets can be widened, and the range of functions of the recording apparatus can also be widened.

It is still another object of the present invention to provide a method of detecting a kind of recording sheet and an apparatus therefor, wherein a light source for emitting light to a recording sheet and a photosensitive element for detecting a light amount are used, amounts of light reflected by the upper and lower surfaces of the recording sheet are detected by the photosensitive elements located at a predetermined position, and the kind of recording sheet is detected based on a difference between the amounts of light reflected by the upper and lower surfaces or one of these amounts of light.

It is still another object of the present invention to provide a method of discriminating the upper surface of a recording sheet from its lower surface, wherein the upper surface of the recording sheet can be automatically discriminated from its lower surface, and reliability of the recording operation can be improved.

It is still another object of the present invention to provide a method of discriminating the upper surface of a recording sheet from its lower surface and an apparatus therefor, wherein a light source for emitting light to a recording sheet and a photosensitive element for detecting a light amount are used, amounts of light reflected by the upper and lower surfaces of the recording sheet are detected by the photosensitive elements located at a predetermined position, and the kind of recording sheet is detected based on a difference between the amounts of light reflected by the upper and lower surfaces.

It is still another object of the present invention to provide a recording apparatus capable of preventing an operation error during recording and widening the application range of the recording sheets when the surface of the recording sheet is reversed.

It is still another object of the present invention to provide a recording apparatus for discriminating the upper surface of a fed recording sheet from its lower surface, wherein when the recording sheet is set in a nonreversed state, recording is performed; and when the recording sheet is reversed, recording is disabled or recording can be started if a printing instruction is input by the user again.

It is still another object of the present invention to provide a control means capable of preventing an operation error of a recording apparatus having a plurality of printing modes and expanding functions of the apparatus.

It is still another object of the present invention to provide a recording apparatus, wherein a kind of recording sheet such as paper, an OHP sheet, or a BPF is designated, the upper surface of a fed recording sheet is discriminated from its lower surface upon detection of states of the upper and lower surfaces of the fed sheet, recording is performed for a standard sheet in a designated recording mode, and recording is inhibited for a nonstandard recording sheet or enabled for the nonstandard recording sheet as needed.

BRIEF DESCRIPTION OF THE DRAWINGS:

FIGS. 5A to 5C are views showing a light transmitting amount detecting means for the recording means;

FIGS. 6-1, 6-1A, 6-1B and 6-2 are flow charts for explaining recording processing method of the recording apparatus shown in FIG. 1; and FIGS. 7-1, 7-1A, 7-1B and 7-2 are flow charts showing another recording processing of the recording apparatus shown in FIG. 1.

Figure 1:
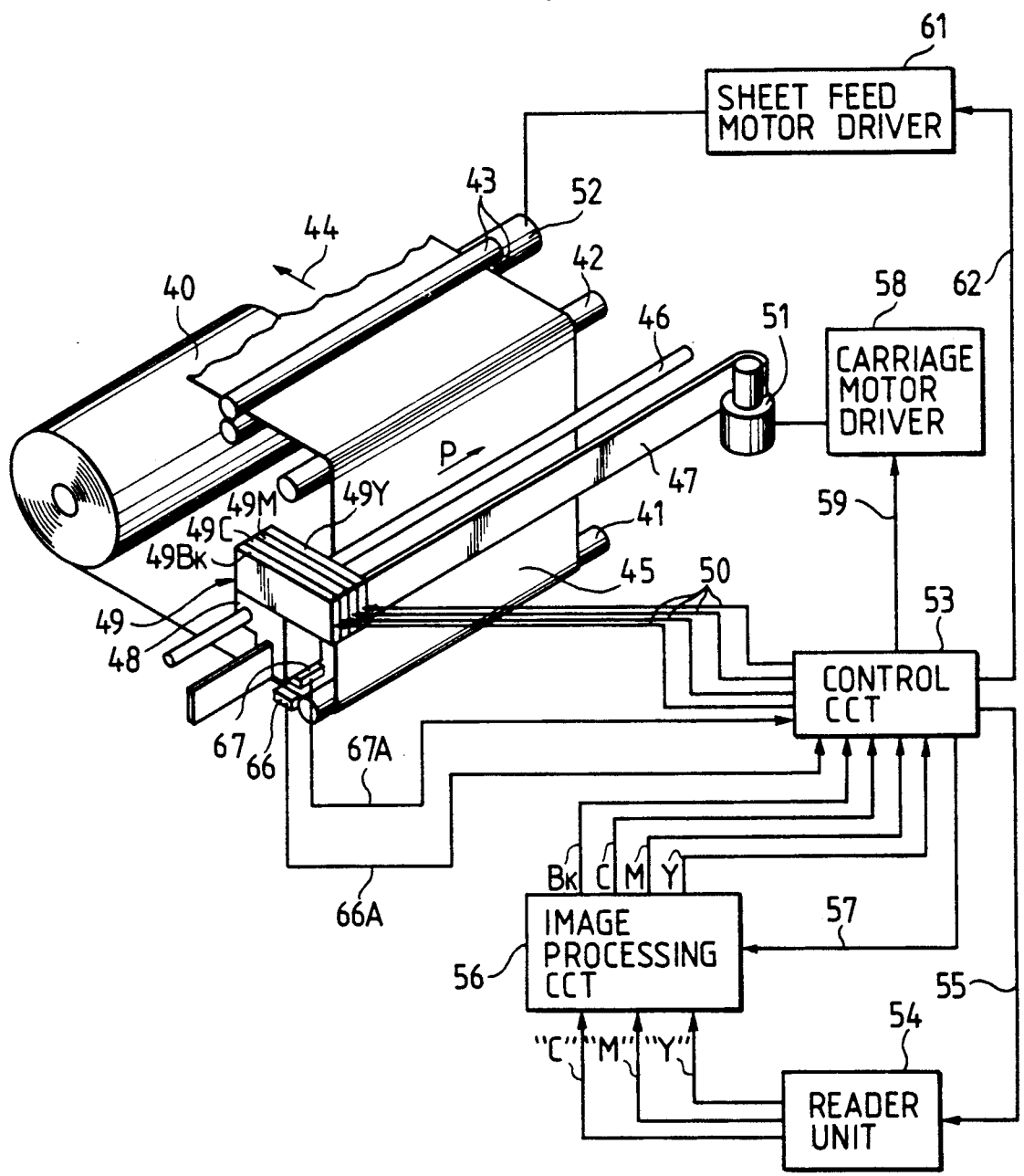
FIG. 1 is a schematic perspective view showing a color ink-jet recording apparatus according to an embodiment of the present invention.
Figure 2:
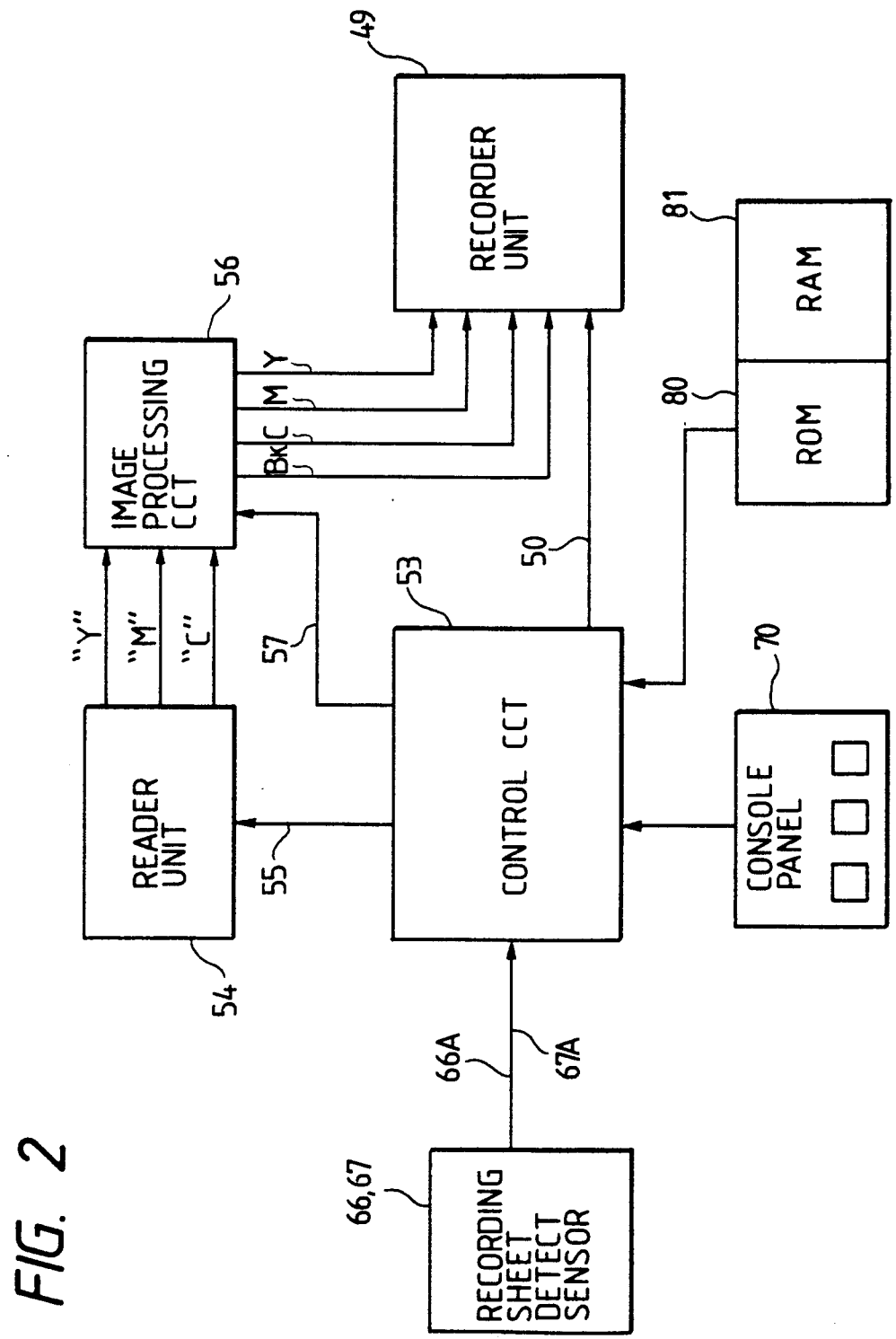
FIG. 2 is a block diagram of a control system in the recording apparatus in FIG. 1.

DETAILED DESCRIPTION OF THE PREFERRED EMBODIMENT:

FIG. 1 is a schematic view showing a color ink-jet recording apparatus according to an embodiment of the present invention, and FIG. 2 is a block diagram of a control system of the recording apparatus shown in FIG. 1.

Referring to FIG. 1, a recording sheet 45 supplied from a sheet roll 40 is conveyed by a frictional force of a feed roller 43 through guide rollers 41 and 42 and is exhausted in a direction indicated by an arrow 44.

A recorder unit including a recording head unit 49 is arranged in front of the front surface of the recording sheet 45 between the upper and lower guide rollers 42 and 41.

A guide shaft 46 parallel to the guide rollers 42 and 41 is disposed in the recorder unit. The color printing head unit 49 is positioned and carried on a carriage 48 which is reciprocated along the guide shaft 46.

The head unit 49 comprises four recording heads, i.e., a yellow head 49Y, a magenta head 49M, a cyan head 49C, and a black head 49Bk. The yellow, magenta, cyan, and black inks are supplied from ink tanks to the heads 49Y, 49M, 49C, and 49Bk, respectively.

The carriage 48 is moved to record and scan the recording sheet 45 with the respective recording heads.

The recording sheet 45 is intermittently fed (line feed) by a printing width of each printing head. The head unit 49 is scanned in a direction indicated by an arrow P to inject ink drops in accordance with an image signal while the recording sheet 45 is kept stopped in the feed direction.

The carriage 48 is reciprocated by a carriage motor (pulse motor) 51 through a timing belt 47, and the feed roller 43 is driven by a sheet feed motor 52.

Referring to FIGS. 1 and 2, a control circuit 53 for controlling carriage operations outputs a reader control signal 55 to a reader unit 54, an image processing control signal 57 to an image processing circuit 56, and recording head control signals 50 to the recording heads 49Y, 49M, 49C, and 49Bk. The control circuit 53 also outputs a carriage motor control signal 59 to a carriage motor driver 58 for driving the carriage motor 51 and a sheet feed motor control signal 62 to a sheet feed motor driver 61 for driving the sheet feed motor 52.

The control circuit 53 comprises a microcomputer for executing programs (FIGS. 6-1, 6-2, 7-1, and 7-2) stored in a ROM 80. The control circuit 53 receives and discriminates signals from sheet sensors 66 and 67 and a console panel 70, causes a RAM 81 to store input data and control data, and outputs control signals.

Ink color data "Y", "M", and "C" from the reader unit 54 are input to and are processed by the image processing circuit 56. The processed signals are input to the control circuit 53 as color image signals Y, M, C, and Bk. The control circuit 53 outputs ink-jet control signals 50 to the recording heads 49Y, 49M, 49C, and 49Bk on the basis of the image signals.

The sensors 66 and 67 for detecting states of the upper and lower surfaces of the recording sheet are arranged at desired positions in the path of the recording sheet 45. Detection signals 66A and 67A from the sensors are supplied to the control circuit 53.

Each of the sensors 66 and 67 comprises a light source for emitting light to the recording sheet 45 and a photosensitive element for detecting an amount of light.

Amounts of light reflected by the upper and lower surfaces of the recording sheet are received by the photosensitive elements located at the predetermined positions. The kind of recording sheet 45 or the upper or lower surface thereof is detected in accordance with the values of the amounts of light reflected by the upper and lower surfaces of the recording sheet 45 or a difference therebetween.

As shown in FIG. 2, the recording apparatus includes the console panel 70 for designating a printing mode (e.g., printing of normal paper, printing of an OHP sheet, printing of a BPF, printing of a real image, or printing of a mirror image) with a touch key and supplying a key input signal to the control circuit 53.

The kinds of recording sheet 45 are paper, an OHP sheet, a BPF, and the like. The states of the upper and lower surfaces of these recording media are as follows.

Paper has rough upper and lower surfaces, and beams reflected by the upper and lower surfaces are scattered beams upon incidence of a beam having high directivity. Therefore, directivity of the incident beam disappears.

The OHP sheet has glossy upper and lower surfaces, and beams reflected by the upper and lower surfaces have high directivity upon incidence of a beam having high directivity.

The BPF has a smooth, glossy upper surface and a rough lower surface. Upon incidence of a beam having high directivity on the upper surface, a beam reflected by the upper surface has high directivity. However, directivity of the incident beam disappears in the beam reflected by the lower surface.

Figure 3A:
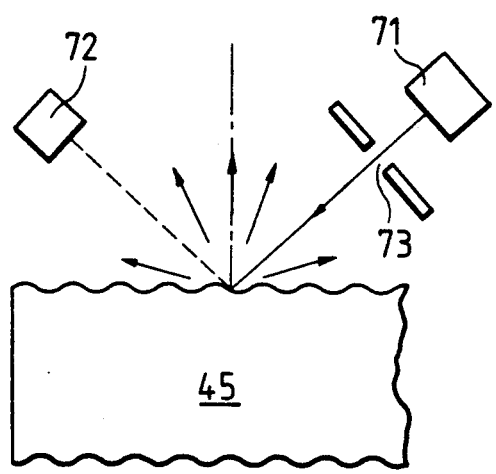
FIGS. 3A to 3C are views showing an optical detecting means for detecting smoothness of a recording sheet.
Figure 3B:
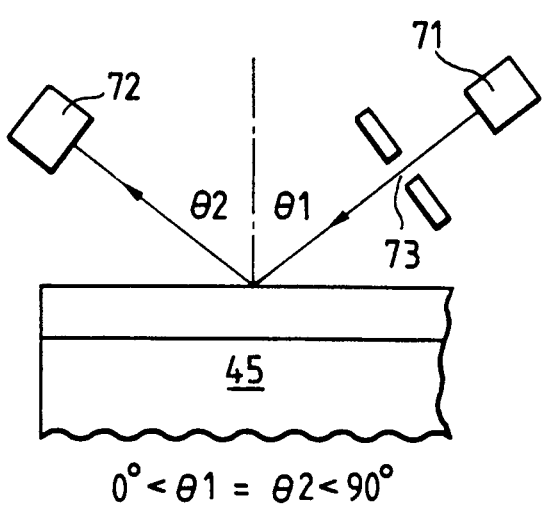
Figure 3C:
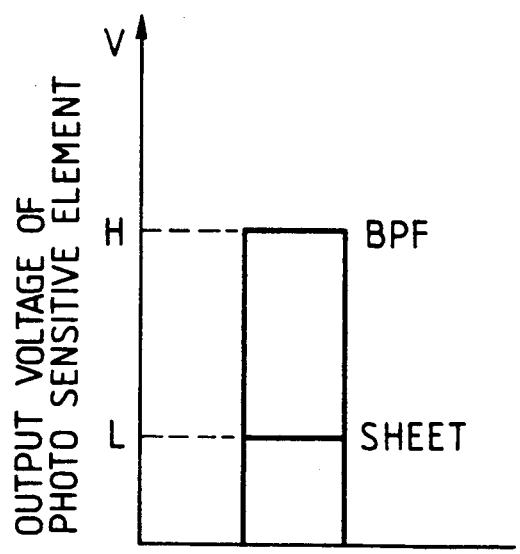

FIGS. 3A and 3B are views showing an arrangement of a sensor for optically detecting rough and smooth surfaces, and FIG. 3C shows characteristics of the sensor.

FIG. 3A shows detection of a rough surface as in that of paper. A beam having high directivity and emitted from a light source 71 through a slit 73 is scattered on the surface of the recording sheet 45, and an amount of beam reflected by the surface and incident on a photosensitive element 72 located on a reflection optical path is reduced to a fraction of the amount of beam emitted from the light source 71.

FIG. 3B shows detection of a smooth surface as in that of the BPF. A beam having high directivity and emitted from the light source 71 is reflected by the surface of the recording sheet 45, and the beam reflected by the surface is incident on the photosensitive element 72 located on the reflection optical path. In this case, the amount of reflected beam is not greatly reduced as compared with the beam emitted from the light source 71 and is kept at a high level.

FIG. 3C shows output voltages of the photosensitive element 72. A voltage level in detection of FIG. 3A exhibits low level L, and a voltage level in detection of FIG. 3B exhibits high level H.

Upon detection of the amounts of reflected beams, states of the surface of the recording sheet 45, i.e., roughness or smoothness of the surface, can be identified.

Figure 4A:
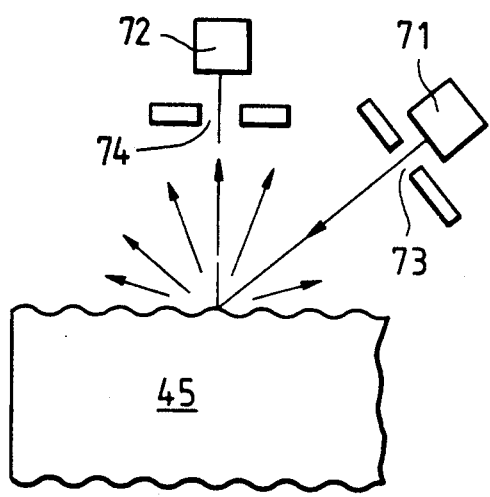
FIGS. 4A to 4C are views showing another optical detecting means for detecting smoothness of a recording means.
Figure 4B:
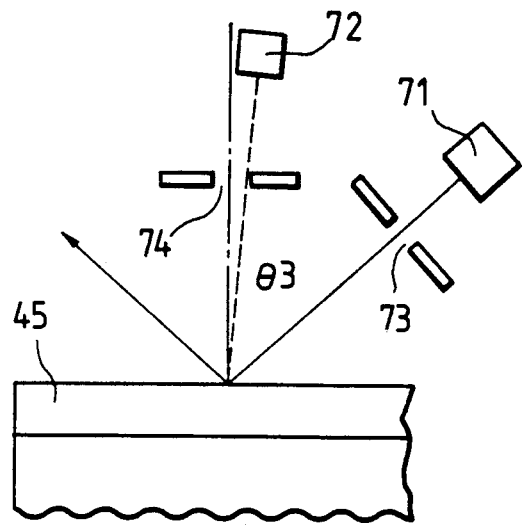
Figure 4C:
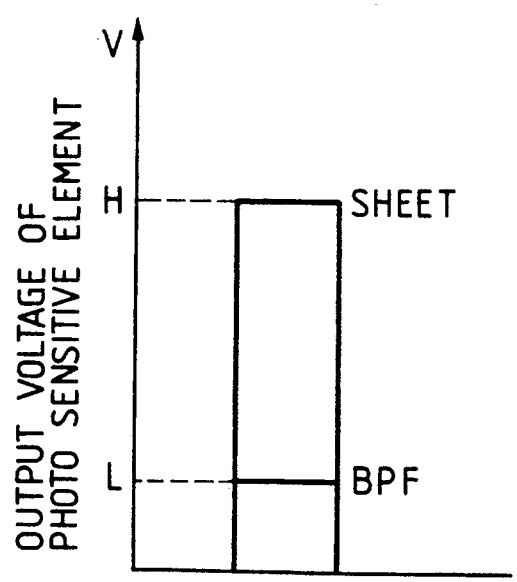

FIGS. 4A to 4B show another sensor for optically detecting rough and smooth surfaces, and FIG. 4C shows characteristics of the sensor.

In the arrangement of FIGS. 4A and 4B, a photosensitive element 72 is offset from a reflection optical path, and a slit 74 is arranged in front of the photosensitive element.

FIG. 4A shows detection of a rough surface as in that of paper or the BPF. A beam having high directivity and emitted from a light source 71 is equally scattered on the upper surface of the recording sheet 45. Therefore, a beam having an amount as a fraction of the amount of the beam emitted from the light source 71 can be incident on the photosensitive element 72 located outside the reflection optical path.

FIG. 4B shows detection of a smooth surface as in that of the BPF or the OHP sheet. A beam having high directivity and emitted from the light source 71 is reflected by the surface of the recording sheet 45, and the reflected beam has high directivity in one direction. In this case, almost no beam is incident on the photosensitive element 72 located outside the reflection optical path.

FIG. 4C is a graph showing output voltages of the photosensitive element 72. Contrary to the arrangement of FIGS. 3A and 3B, an output voltage corresponding to the rough surface in detection of FIG. 4A is set to high level H, and an output voltage corresponding to the smooth surface in detection of FIG. 4B is set to low level L.

According to the method shown in FIGS. 4A to 4C, the amount of reflected beam is detected to identify that the surface of the recording sheet 45 is rough or smooth.

According to the recording sheet detecting means 66 and 67, the kind of recording sheet 45, i.e., paper, an OHP sheet, or a BPF can be identified.

For example, a recording sheet having rough upper and lower surfaces is identified as paper. A recording sheet having smooth upper and lower surfaces is identified as an OHP sheet. A recording sheet having a smooth upper surface and a rough lower surface is identified as a BPF.

When two kinds of recording sheets, i.e., paper and an OHP sheet are discriminated from each other, or when surfaces of paper and a BPF are discriminated from each other, roughness of one of the surfaces determines the kind of recording sheet 45. In this case, only one of the recording sheet detecting means 66 and 67 is used.

The recording sheet detecting means 66 and 67 can discriminate the upper surface of the recording sheet 45 from its lower surface.

For example, if the recording sheet 45 is a BPF, whether the upper or lower surface is properly set can be detected on the basis of a difference between the amounts of light reflected by the upper and lower surfaces, i.e., on the basis of whether the amount of reflected light detected by the method of FIGS. 3A to 3C or FIGS. 4A to 4C is high or low level H or L.

The upper or lower surface of the fed recording sheet 45 can be detected by the control system shown in FIGS. 1 and 2. If the side of the recording sheet is appropriate, recording is performed. However, if the side of the recording sheet is reversed, recording is inhibited or allowed upon a reinstruction by a user in accordance with the kind of recording sheet 45. These operations are performed by executing control programs.

The above control system is incorporated in the recording apparatus, and the kind of recording sheet 45 and its side, i.e., upper or lower surface, can be automatically detected, thereby eliminating operation errors.

The printing enable and disable modes can be classified by the recording (printing) modes such as a real image printing mode, a mirror image printing mode, and a BPF printing mode even if the side of the recording sheet is reversed. According to the above control system, a printing enable, nonstandard state is determined by the detection signals from the sensors 66 and 67, and a message representing the printing enable, nonstandard state is displayed. A printing enable mode can be set if the user instructs it again. Therefore, operation errors during recording can be prevented, and the range of selection of recording sheets can be widened, thereby improving performance of the recording apparatus.

FIGS. 5A and 5B show a method in which a light source 71 and a photosensitive element 72 oppose each other through the recording sheet 45, and the kind of recording sheet 45 is detected in accordance with an amount of light transmitted through the recording sheet 45, and FIG. 5C shows characteristics of the sensor.

FIG. 5A shows detection when a recording sheet is an opaque sheet such as paper and an amount of beam transmitted through the opaque sheet is small. FIG. 5B shows detection when a recording sheet is a transparent sheet such as a BPF or OHP sheet and an amount of beam transmitted through the transparent sheet is large.

FIG. 5C is a graph showing output voltage levels of the photosensitive element. When the recording sheet is opaque as in FIG. 5A, the amount of beam transmitted through the opaque sheet is small, and an output voltage of the photosensitive element 72 is set at low level L. However, when the recording sheet is transparent as in FIG. 5B, the amount of beam transmitted through the transparent sheet is large, and an output voltage of the photosensitive element 72 is set at high level H.

When the control system and the optical detecting means which have been described with reference to FIGS. 1 to 5C are used, the following recording apparatus can be arranged. It should be noted that an ultrasonic generator and an ultrasonic receiver are arranged in the same manner a in the optical detecting means described above to obtain the same effect as described above.

The kind of recording sheet 45 (e.g., paper, an OHP sheet, or a BPF) fed to the recording apparatus is designated. The states (smoothness) of the upper and lower surfaces of the fed recording sheet 45 are detected to discriminate the kind of recording sheet 45 and its side. If the discriminated sheet is a standard sheet in the designated recording mode, recording is performed. Otherwise, the recording sheet is discriminated as a nonstandard sheet in the designated recording (printing) mode. In this case, recording is inhibited or allowed by an instruction by the user again, thus providing a recording sheet designation type recording apparatus.

A mode designation type recording apparatus having another arrangement can be proposed. A mode such as a real image mode, a mirror image mode, or a BPF mode is detected, and the side of the recording sheet is then detected. If the detected recording sheet is a standard sheet in the designated recording mode, recording is performed. If the detected recording sheet is a nonstandard sheet but image formation can be performed, an image is output, and if the user instructs printing again, the image is recorded (printed).

Figures 1A, 6:
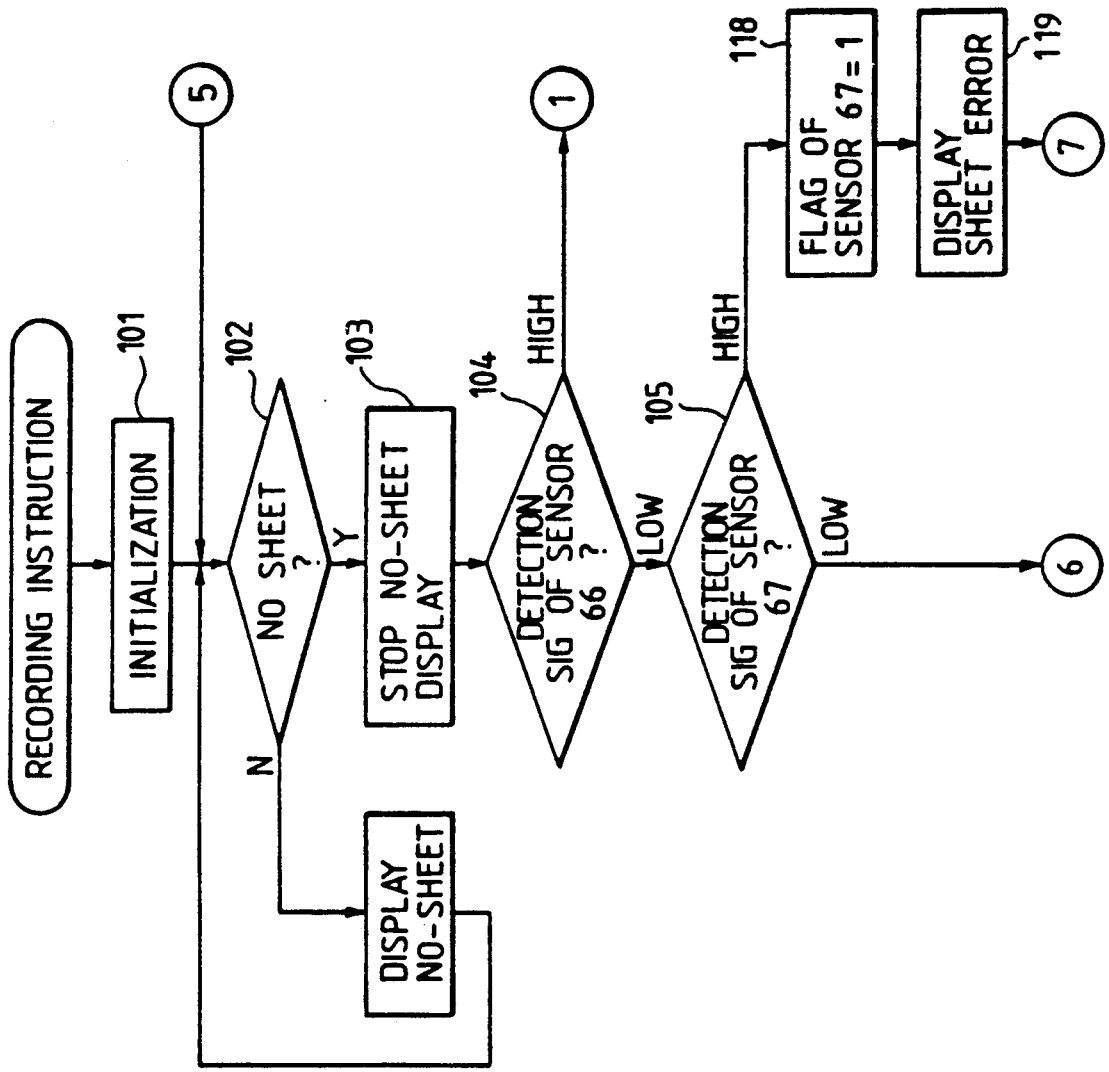
Figures 1, 6:
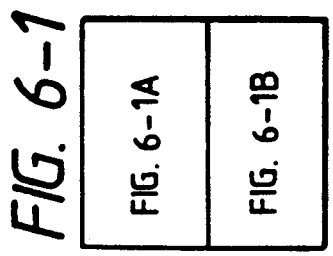
Figures 1B, 6:
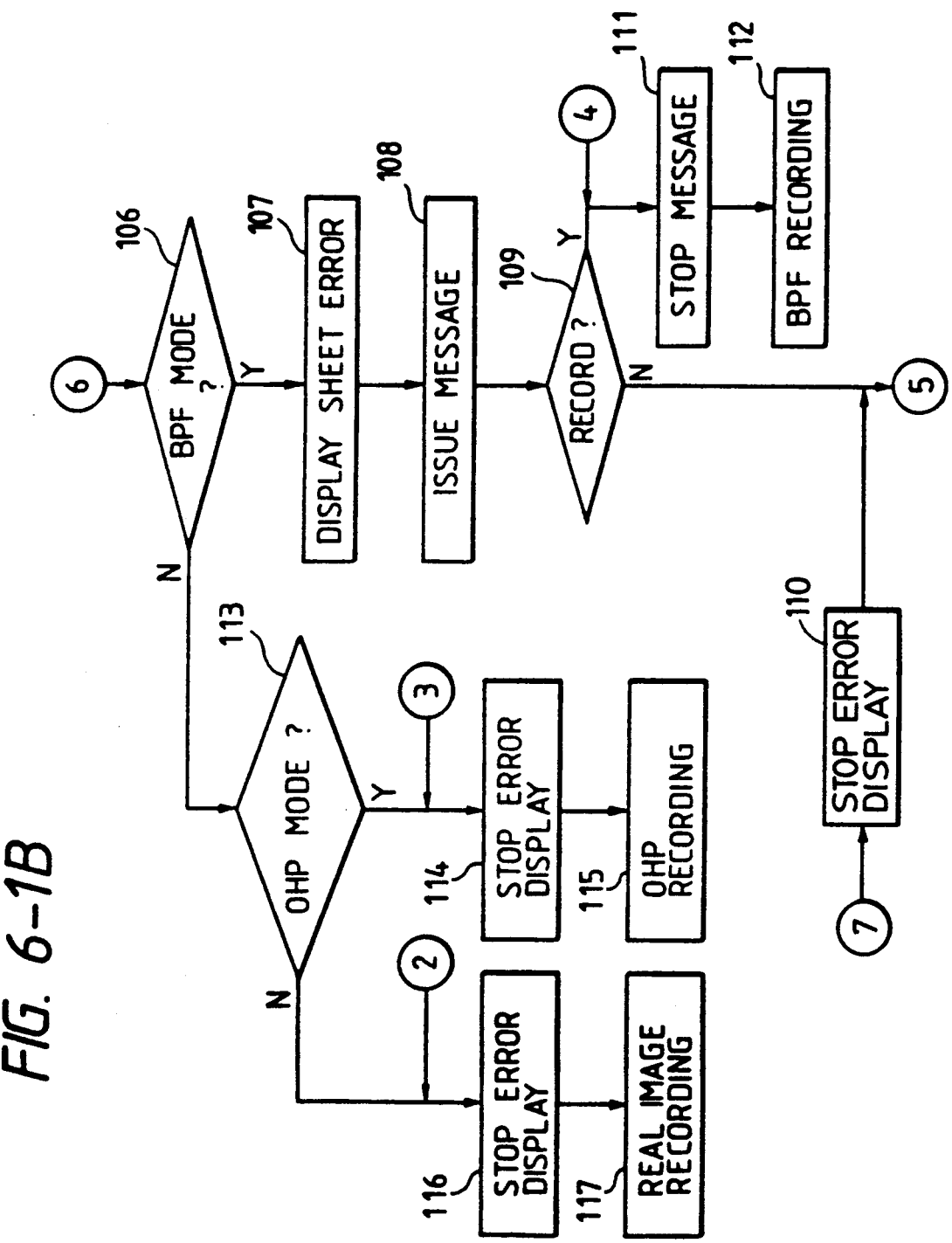
Figures 2, 6:
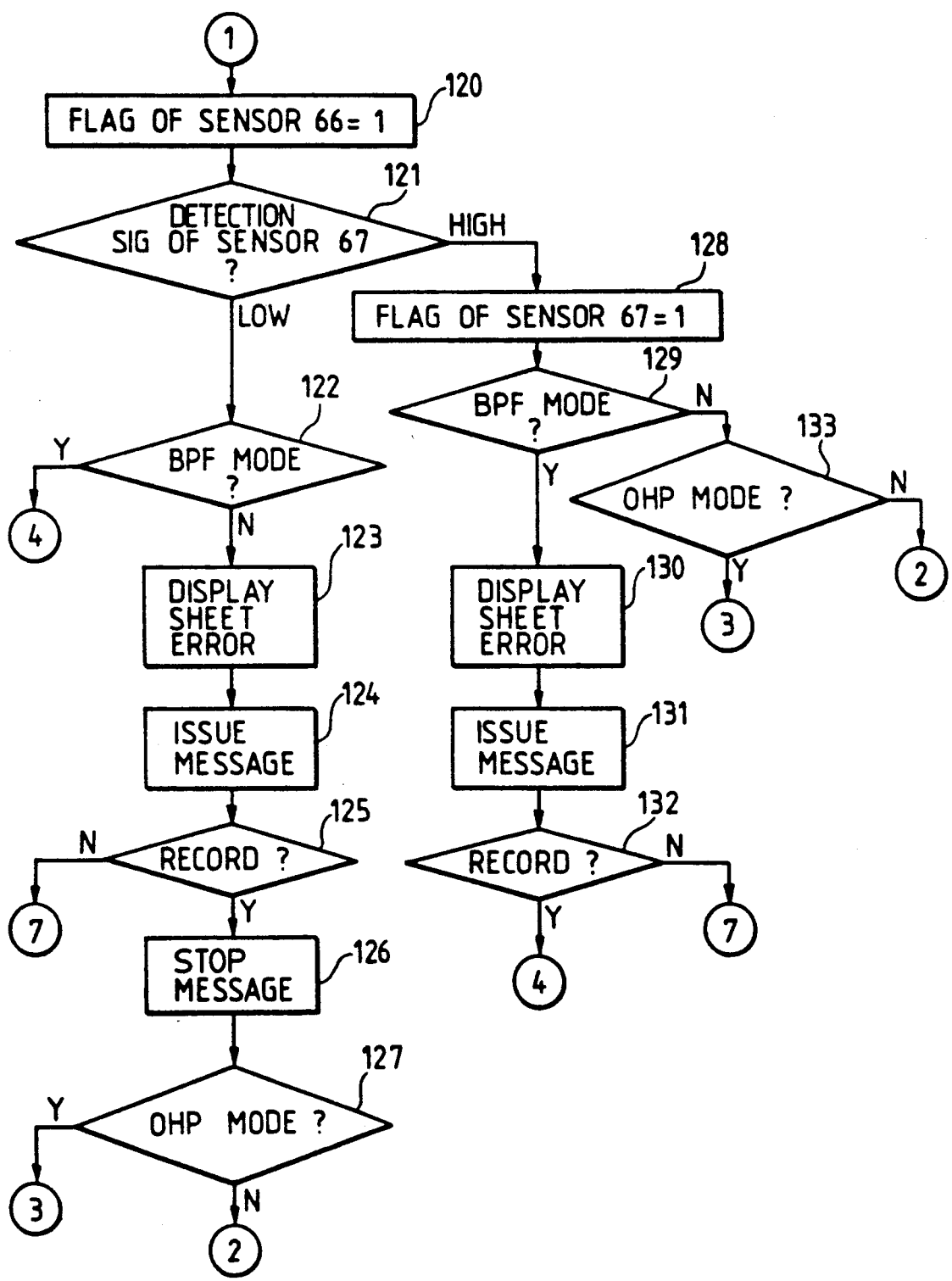
Figures 1A, 7:
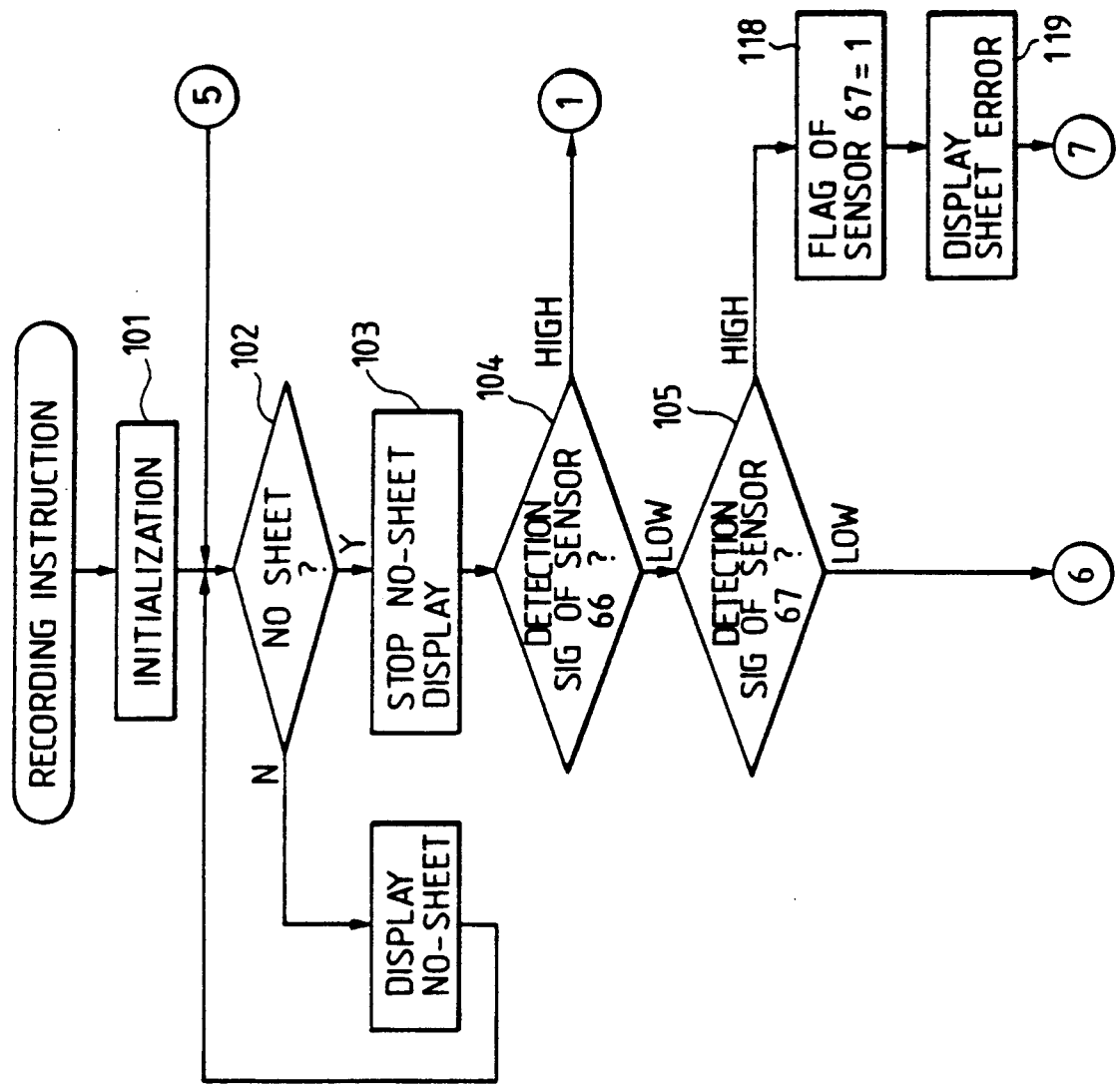
Figures 1, 7:
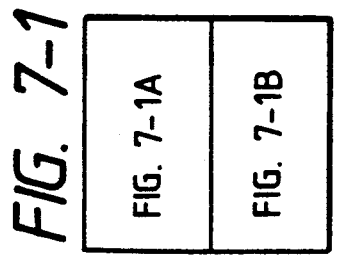
Figures 1B, 7:
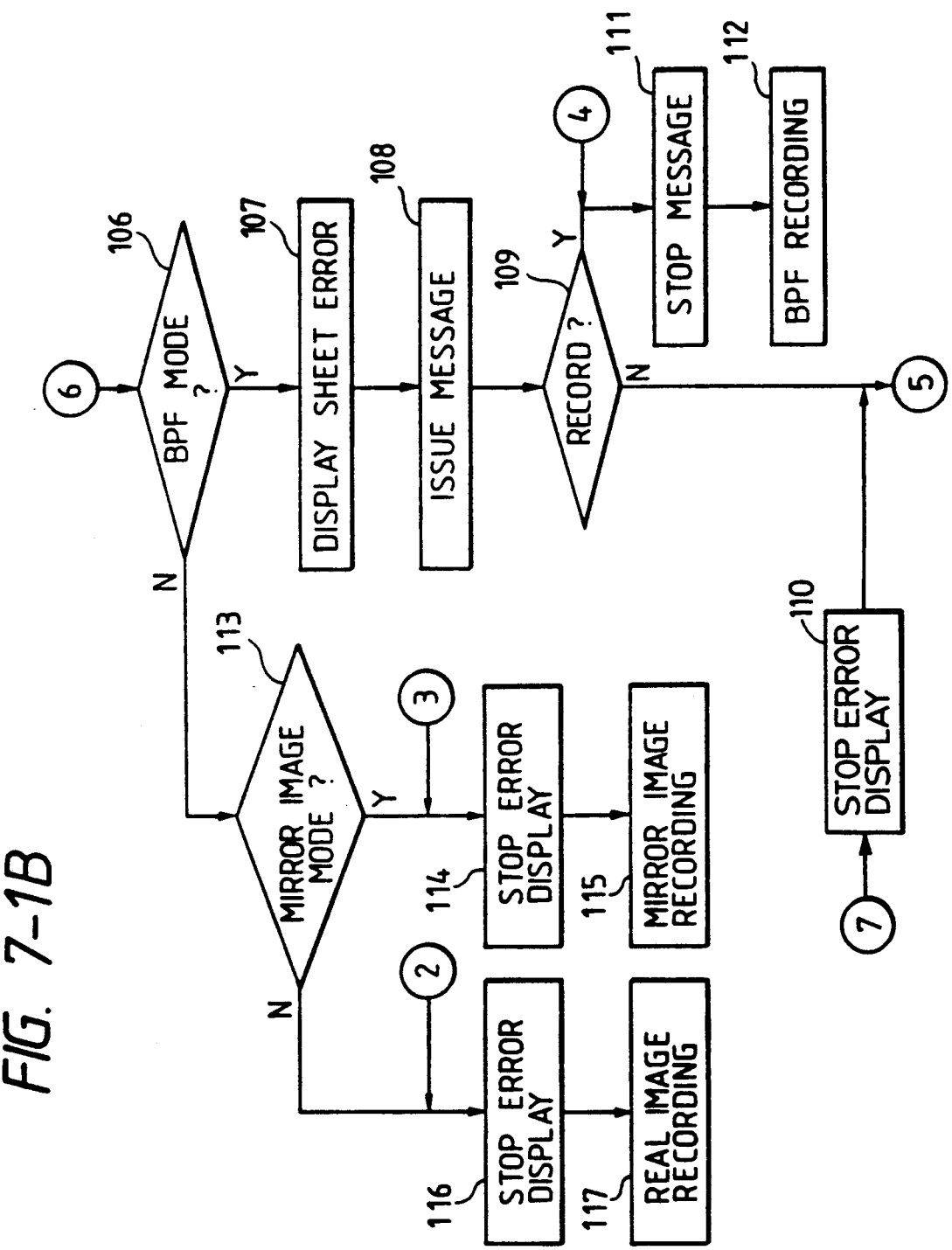
Figures 2, 7:
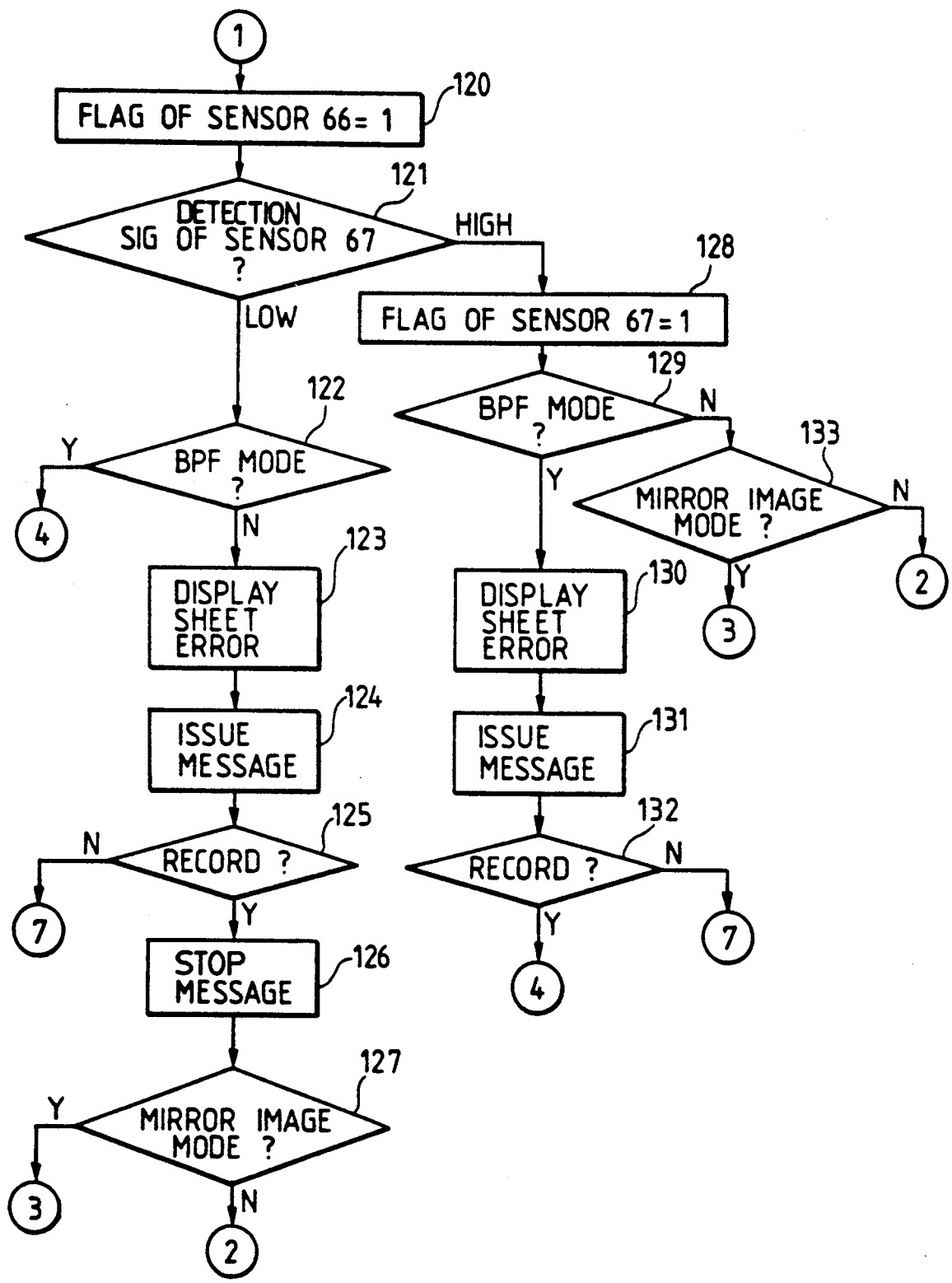

FIGS. 6-1 and 6-2 are flow charts for explaining an operation of the recording sheet designation type recording apparatus, and FIGS. 7-1 and 7-2 are flow charts for explaining an operation of the printing mode designation type recording apparatus.

In the flow charts, a recording instruction and a recording mode are input by key switches in the console panel 70 (FIG. 2). An input mode signal is stored in the RAM 81. Mode determination in step 106 or the like is performed by determining the content of the mode data stored in the RAM 81.

Referring to FIGS. 6-1 and 6-2, when the recording instruction is input, initialization is performed, i.e., flags of the sensors 66 and 67 are reset to zero in step 101, and various display contents are cleared. In step 102, the presence/absence of the recording sheet 45 is determined. If there is no sheet in step 102, display a message "NO-SHEET".

However, if there is a recording sheet 45 in step 102, the "NO-SHEET" display is stopped in step 103. In step 104, the smoothness of the upper surface of the recording sheet 45 is detected by the upper surface detection sensor (detecting means) 66 on the basis of an amount of beam reflected by the upper surface.

If the sensor 66 detects that the upper surface is rough, i.e., a sensor output is low, the flow advances to step 105. Smoothness of the lower surface of the recording sheet 45 is detected by the lower surface detection sensor 67 on the basis of the amount of beam reflected by the lower surface.

If a sensor output is low, i.e., the sensor 67 detects that the lower surface is rough, the control circuit 53 determines that a sheet having rough upper and lower surfaces, i.e., paper, is inserted. In this case, the flow advances to step 106 to determine whether the recording mode of the recording apparatus is set in the BPF mode.

If YES in step 106, the sheet both surfaces of which are rough is not a standard sheet (BPF) in this mode. In step 107, an error display is performed. An interrogation display (message) is output in step 108.

In this case, the message is given such that "set a proper sheet or a proper printing mode again, or instruct recording since recording can be performed although image colors are slightly changed".

In step 109, the control circuit 53 determines based on the instruction of the user whether recording is performed. If NO in step 109, the flow returns to step 102. Determination of the reinstruction for recording is based on that of the above-mentioned recording instruction input by a key switch.

If recording is instructed in step 109, the flow advances to step 111, and the message is stopped in step 111. In step 112, recording is performed in the BPF recording (printing) mode.

However, if NO in step 106, the flow advances to step 113 to determine whether the OHP recording mode is set, i.e., whether the mode using an OHP sheet is set. If YES in step 113, an error display is stopped in step 114. Recording is performed in the OHP recording (printing) mode in which the detected sheet is not a standard sheet (step 115).

If NO in step 113, the control circuit 53 determines that the normal recording (printing) mode using the normal paper as the standard sheet is set. The error display is stopped in step 116. In step 117, real image recording processing is performed for the normal paper in the normal printing mode.

When the sensor 67 detects in step 105 that the lower surface is smooth, the control circuit 53 determines that the detected sheet has a rough upper surface and a rough lower surface, so that the BPF is inserted with the upper surface facing down (reversed state). In this case, image formation cannot be performed. In step 118, a flag of the lower surface sensor 67 is set, and the flow advances to step 119. In step 119, a sheet error display is performed, and recording is not performed. The flow advances to step 110, and the interrogation display (message) is stopped. The flow then returns to step 102.

When the control circuit 53 determines in step 104 that the upper surface is smooth, the flag of the upper surface sensor 66 is set in step 120. The control circuit 53 determines in step 121 whether the lower surface is smooth or rough by the sensor 67.

If the lower surface is detected to be rough by the sensor 67, the control circuit 53 determines that a recording sheet (BPF) having a smooth upper surface and a rough lower surface is inserted. The flow advances to step 122 to determine whether the printing mode is the BPF mode. If YES in step 122, the detected sheet is the standard recording sheet. The flow advances to step 111 to stop displaying the interrogation (message). Recording is performed in the BPF mode in step 112.

If NO in step 122, i.e., the printing mode is determined not to be the BPF printing mode, the BPF is erroneously inserted. In step 123, the sheet error display is performed, and the interrogation display (message display) is performed in step 124. The user instructs in step 125 whether recording is performed.

If recording is not performed, the flow advances to step 110, and the message display is stopped. The flow then returns to step 102, and the above operations are repeated.

When a recording instruction is input in step 125, the message display is stopped in step 126. The flow advances to step 127 to determine whether the OHP printing mode is set.

If YES in step 127, the flow returns to step 114 to stop the error display. In step 115, recording is performed in the OHP printing mode in which image formation can be performed although not on a standard sheet.

If NO in step 127, i.e., when the OHP printing mode is not set, the flow returns to step 116 to stop the error display. In step 117, recording is performed in the normal paper recording (printing) mode in which image formation can be performed although not on a standard sheet.

When the control circuit 53 determines in step 121 that the lower surface is also smooth, the flow advances to step 128 to set the flag of the lower surface sensor 67. The control circuit 53 determines in step 129 whether the printing mode is the BPF mode.

Since the upper and lower surfaces of the sheet are smooth, the sheet is an OHP sheet. The OHP sheet is erroneously inserted if the mode is the BPF printing mode. A sheet error display is performed in step 130, and an interrogation (message) display is performed in step 131. The user instructs in step 132 whether recording is performed in an image formation enable mode although the OHP sheet is not a standard sheet in this mode.

If a printing instruction is input by the user, the flow advances to step 111 to stop the interrogation (message) display. In step 112, recording is performed in the BPF printing mode.

However, if the printing instruction is not input by the user in step 132, the flow returns to step 102, and the above operations are repeated.

When the printing mode is determined not to be the BPF printing mode in step 129, the flow advances to step 133 to determine whether the printing mode is the OHP printing mode.

If YES in step 133, it is determined that the standard sheet is inserted as the recording sheet 45, and the flow advances to step 114 to stop the error display. In step 115, printing is then performed in the OHP printing mode.

However, if NO in step 133, i.e., the printing mode is determined not to be the OHP printing mode, the printing mode of the normal paper is supposed to be set. The flow returns to step 116 to stop the error display. Recording on the normal paper is performed in the real image printing mode in step 117.

Recording operations of the recording sheet designating type recording apparatus for designating recording sheets such as paper, an OHP sheet, and a BPF are controlled by the operation procedures in FIGS. 6-1 and 6-2 described above.

Operations of the recording (printing) mode designation type recording apparatus will be described with reference to FIGS. 7-1 and 7-2. In steps 113, 127, and 133 of the flow charts of FIGS. 6-1 and 6-2, the control circuit 53 determines whether the recording mode is set in the recording (printing) mode using the OHP sheet. However, in steps 113, 127, and 133 of the flow charts of FIGS. 7-1 and 7-2, the control circuit 53 determines whether the printing mode is set in the mirror image mode (not the real image mode). Other operations in FIGS. 7-1 and 7-2 are substantially the same as those in FIGS. 6-1 and 6-2.

More specifically, in step 106 of FIGS. 7-1, when the printing mode is determined not to be the BPF recording mode, the flow advances to step 113 to determine whether the mirror image recording (printing) mode is set. If the printing mode is determined not to be the real image printing mode but the mirror image printing mode, the error display is stopped in step 114. In step 115, recording is performed in the mirror image recording (printing) mode in which image formation can be performed but is not standard.

When the control circuit 53 determines in step 113 that the mirror image printing mode is not set, it determines that the normal recording (printing) mode using the normal paper as a standard sheet is set. In step 116, the error display is stopped, and recording is performed on the normal paper in the normal real image printing mode in step 117.

When a recording instruction is input in step 125, the flow advances to step 126 to stop the error message. The flow advances to step 127 to determine whether the OHP printing mode is set.

If the mirror image printing mode is designated, the flow returns to step 114 to stop the error display. In step 115, recording is performed in the mirror image printing mode in which image formation can be performed but is not standard. However, if NO in step 127, the flow returns to step 116 to stop error display. In step 117, recording is performed in the normal paper real image recording (printing) mode.

When the control circuit 53 determines in step 129 that the printing mode is not the BPF printing mode, the flow advances to step 133 to determine whether the printing mode is the mirror image printing mode.

If YES in step 133, the standard sheet (OHP sheet) is inserted in the mirror image printing mode. In this case, the flow advances to step 114 to stop the error display. Recording is performed in the mirror image printing mode in step 115.

However, if NO in step 133, the normal paper real image printing mode is supposed to be set. In this case, the flow returns to step 116 to stop the error display. Recording is performed in the real image printing mode in step 117.

The recording operations of the recording (printing) mode designation type recording apparatus for designating the real image printing mode, the mirror image printing mode, and the BPF printing mode are controlled by the operation procedures described in FIGS. 7-1 and 7-2.

The present invention is also applicable to a thermal or wire-dot recording apparatus in addition to the ink-jet recording apparatus.

What is claimed is:

1. A printing apparatus comprising:
   printing means for forming an image on a recording sheet;
   means for detecting an upper or lower surface of the recording sheet; and
   means for determining, according to a detection result of said detecting means, a recording enable state when the upper and lower surfaces of the recording sheet are properly set and a recording disable state when the upper and lower surfaces of the recording sheet are reversed.

2. A printing apparatus comprising:
   printing means for forming an image on a recording sheet;
   means for designating different printing modes;
   means for detecting an upper or lower surface of the recording sheet or a type of the recording sheet; and
   means for determining whether or not the surface of the recording sheet or the type of the recording sheet is proper in a mode designated by said mode designating means in accordance with a detection result of said detecting means.

3. An apparatus according to claim 1, further including input means for allowing printing even if the surface of the recording sheet is improper.

4. An apparatus according to claim 2, further including input means for allowing printing even if the surface of the recording sheet or the type of the recording sheet is improper in a mode designated by said mode designating means.

5. An apparatus according to claim 1, further including input means for allowing printing even if the surface of the recording sheet is improper and outputting a message representing that the surface of the recording sheet is improper.

6. An apparatus according to claim 2, further including input means for allowing printing even if the surface of the recording sheet or the type of the recording sheet is improper and outputting a message representing that the surface of the recording sheet or the type of the recording sheet is improper.

* * * * *

UNITED STATES PATENT AND TRADEMARK OFFICE
CERTIFICATE OF CORRECTION

PATENT NO.   :   5,004,928
DATED        :   April 2, 1991
INVENTOR(S)  :   Akio Suzuki, et al.

It is certified that error appears in the above-identified patent and that said Letters Patent is hereby corrected as shown below:

COLUMN 3

Line 63, "are," should read --are--; and

Line 67, "processing of" should read --processing method of--.

COLUMN 7

Line 38, "a" should read --as--.

COLUMN 12

Lines 19 and 24, "input means" should read --means--.

Signed and Sealed this

Sixteenth Day of February, 1993

Attest:

STEPHEN G. KUNIN

*Attesting Officer*       *Acting Commissioner of Patents and Trademarks*